(12) United States Patent
Hashimoto et al.

(10) Patent No.: US 9,918,616 B2
(45) Date of Patent: Mar. 20, 2018

(54) MEDICAL DEVICE

(71) Applicant: OLYMPUS CORPORATION, Tokyo (JP)

(72) Inventors: Tatsutoshi Hashimoto, Tokyo (JP); Shotaro Takemoto, Tokyo (JP); Nobuko Matsuo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/937,567

(22) Filed: Nov. 10, 2015

(65) Prior Publication Data
US 2016/0135666 A1 May 19, 2016

Related U.S. Application Data

(63) Continuation of application No. PCT/JP2014/067558, filed on Jul. 1, 2014.
(Continued)

(51) Int. Cl.
*A61B 1/00* (2006.01)
*A61B 1/005* (2006.01)
(Continued)

(52) U.S. Cl.
CPC ........ *A61B 1/00098* (2013.01); *A61B 1/0051* (2013.01); *A61B 1/0057* (2013.01);
(Continued)

(58) Field of Classification Search
CPC .............. A61B 1/0008; A61B 1/00087; A61B 1/00089; A61B 1/00098; A61B 1/00131;
(Continued)

(56) References Cited

U.S. PATENT DOCUMENTS

| 4,245,624 A | 1/1981 | Komiya |
| 2008/0051631 A1* | 2/2008 | Dejima ................ A61B 1/0052 600/114 |

(Continued)

FOREIGN PATENT DOCUMENTS

| JP | S61-268225 A | 11/1986 |
| JP | H05-307143 A | 11/1993 |

(Continued)

OTHER PUBLICATIONS

Mar. 1, 2017 Extended European Search Report issued in European Patent Application No. 14834161.3.
(Continued)

*Primary Examiner* — Ryan Henderson
(74) *Attorney, Agent, or Firm* — Oliff PLC

(57) ABSTRACT

A medical device includes a long shaft member, a curved portion configured to be curved, a support member that is configured to be deformed along a curved shape of the curved portion, a guide member that extends from a distal end of the curved portion, and a linear member that includes a connection portion connected to the guide member, the linear member being inserted into the support member, and that pulls the guide member in accordance with a change of the curved shape. A central axis of the guide member is positioned apart from the central axis of the support member. The linear member which protrudes from the support member is inclined with respect to a longitudinal axis of the guide member and is connected to the connection portion.

7 Claims, 8 Drawing Sheets

Related U.S. Application Data

(60) Provisional application No. 61/864,108, filed on Aug. 9, 2013.

(51) Int. Cl.
*A61B 17/00* (2006.01)
*A61M 25/01* (2006.01)
*A61B 1/018* (2006.01)
*A61B 17/29* (2006.01)

(52) U.S. Cl.
CPC .......... *A61B 1/00131* (2013.01); *A61B 1/018* (2013.01); *A61B 17/00234* (2013.01); *A61M 25/0133* (2013.01); *A61M 25/0147* (2013.01); *A61B 1/005* (2013.01); *A61B 1/00135* (2013.01); *A61B 17/29* (2013.01); *A61B 2017/0034* (2013.01); *A61B 2017/00269* (2013.01); *A61B 2017/00296* (2013.01); *A61B 2017/00323* (2013.01)

(58) Field of Classification Search
CPC ............ A61B 1/00135; A61B 1/00142; A61B 1/00154; A61B 1/005; A61B 1/008; A61B 1/01; A61B 2017/003; A61B 2017/00305; A61B 2017/00309; A61B 2017/00314; A61B 2017/00318; A61B 2017/00323; A61B 2017/00327; A61B 2017/00331; A61M 25/0133; A61M 25/0136; A61M 25/0138; A61M 25/0141; A61M 25/0144; A61M 25/0147; A61M 25/0152
USPC ........ 600/104, 106, 107, 114–115, 121–125, 600/127, 129, 139–152
See application file for complete search history.

(56) References Cited

U.S. PATENT DOCUMENTS

2009/0036736 A1* 2/2009 Dejima ................ A61B 1/0052
600/106
2011/0118543 A1* 5/2011 Dosher .............. A61B 17/3421
600/104

FOREIGN PATENT DOCUMENTS

| JP | H07-8450 A | 1/1995 |
| JP | 2012-161454 A | 8/2012 |

OTHER PUBLICATIONS

Sep. 22, 2014 International Search Report issued in International Patent Application No. PCT/JP2014/067558.

* cited by examiner

MEDICAL DEVICE

This application is a continuation application based on a PCT International Application No. PCT/JP2014/067558, filed on Jul. 1, 2014, whose priority is claimed on U.S. Provisional Patent Application No. 61/864,108, filed Aug. 9, 2013, the content of the PCT International Application and the US Provisional Patent Application are incorporated herein by reference.

BACKGROUND OF THE INVENTION

Field of the Invention

The present invention relates to a medical device. More specifically, the present invention relates to an endoscopic overtube and an endoscope device.

Description of Related Art

Attaching a treatment tool to an endoscope and treating a human body is known. For example, a Japanese Unexamined Patent Application, First Publication No. H7-8450 discloses an endoscope having a function of changing a direction of a treatment tool.

SUMMARY OF THE INVENTION

According to a first aspect of the present invention, a medical device includes a long shaft member configured to be inserted into a body; a curved portion that is disposed at a distal end of the long shaft member to be able to be curved; a support member that has a space extending along a longitudinal axis of the curved portion and that is configured to be deformed along a curved shape of the curved portion; a guide member that extends from a distal end of the curved portion on an axis line substantially parallel to a central axis of the support member and that has a space into which a treatment tool is able to be inserted; and a linear member that includes a connection portion connected to the guide member, the linear member being inserted into the space of the support member to be movable relative to the curved portion, and that pulls the guide member in accordance with a change of the curved shape. A central axis of the guide member is positioned apart from the central axis of the support member. The linear member which protrudes from the support member is inclined with respect to a longitudinal axis of the guide member.

According to a second aspect of the present invention, in the medical device according to the first aspect, the support member may include a first support member that has a first space extending along the longitudinal axis of the curved portion and configured to be deformed along the curved shape of the curved portion, and a second support member that has a second space extending along the longitudinal axis of the curved portion and configured to be deformed along the curved shape of the curved portion. The linear member may include a first linear member that includes a first connection portion connected to the guide member, the first linear member being inserted into the first space to be movable relative to the curved portion, and that pulls the guide member in accordance with a change of the curved shape, and a second linear member that includes a second connection portion connected to the guide member, the second linear member being inserted into the second space to be movable relative to the curved portion, and that pulls the guide member in accordance with a change of the curved shape. The central axis of the guide member may be positioned apart from the central axis of the first support member and the central axis of the second support member. The first linear member which protrudes from the first support member may be inclined with respect to the longitudinal axis of the guide member. The second linear member which protrudes from the second support member may be inclined with respect to the longitudinal axis of the guide member.

According to a third aspect of the present invention, in the medical device according to the first aspect, the long shaft member may have a tube shape.

According to a fourth aspect of the present invention, in the medical device according to the first aspect, the long shaft member may be an insertion section of an endoscope device.

According to a fifth aspect of the present invention, in the medical device according to the first aspect, the guide member may be an extension tube member that has an outer diameter smaller than an outer diameter of the curved portion and being formed in a tube shape. The distal end of the linear member may be fixed to an outer side surface of the extension tube member.

According to a sixth aspect of the present invention, in the medical device according to the second aspect, the first support member may be disposed along the longitudinal axis of the curved portion at a first position which is separated outward in a radial direction of the guide member from an outer side surface of the guide member. The second support member may be disposed along the longitudinal axis of the curved portion at a second position which is different from the first position and which is separated outward in the radial direction of the guide member from the outer side surface of the guide member. A distance between the first connection portion and the second connection portion may be smaller than a distance between the first position and the second position in a virtual cross-section of the curved portion perpendicular to the longitudinal axis of the curved portion.

DETAILED DESCRIPTION OF THE INVENTION (First Embodiment)

Figure 1:
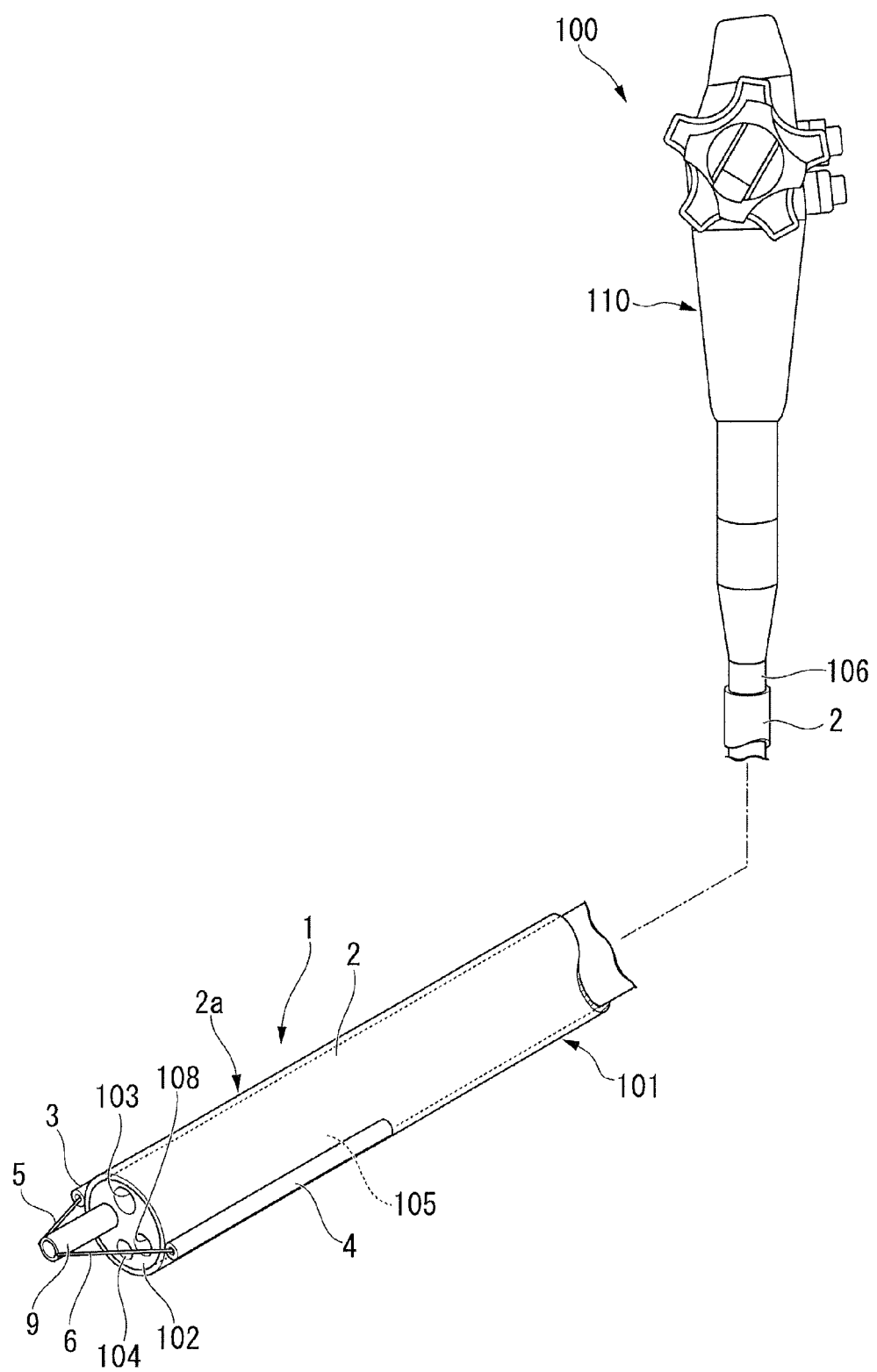
FIG. 1 is a general view showing an endoscope device to which an overtube as a medical device according to a first embodiment of the present invention is attached.
Figure 2:
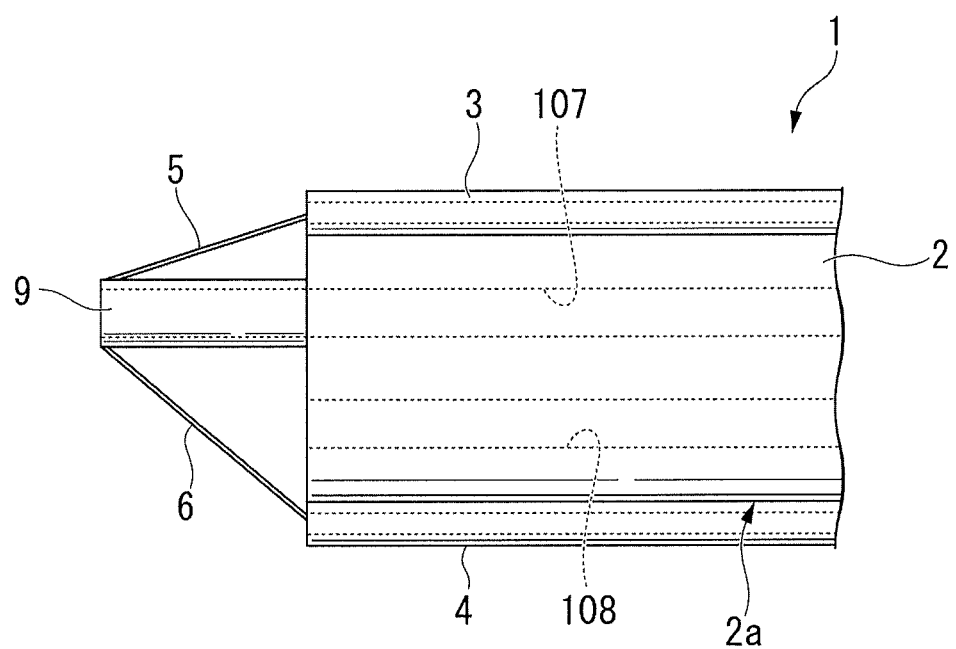
FIG. 2 is an enlarged view of a distal end of the overtube.
Figure 3:
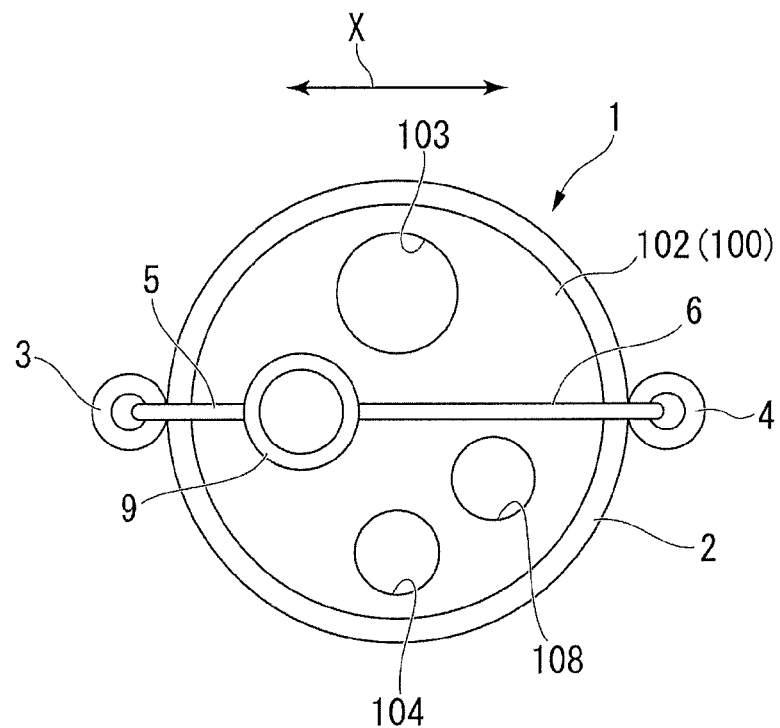
FIG. 3 is a front view of the overtube.

A first embodiment of the present invention will be described below. FIG. 1 is a general view showing an overtube 1 as a medical device according to the first embodiment of the present invention. FIG. 2 is an enlarged view of a distal end of the overtube 1. FIG. 3 is a front view of the overtube 1.

The overtube 1 according to this embodiment can be attached to an endoscope device 100 shown in FIG. 1.

The endoscope device 100 to which the overtube 1 according to this embodiment is attached is, for example, a so-called front view endoscope device 100. For example, as shown in FIG. 1, the front view endoscope device 100 to which the overtube 1 is attached includes an insertion section 101 which is inserted into a body and a manipulation section 110 which is connected to the insertion section 101.

The insertion section 101 includes a tip constructing portion 102, a curving mechanism 105, and a flexible tube portion 106. The tip constructing portion 102, the curving mechanism 105, and the flexible tube portion 106 are arranged in this order and are connected to each other. As shown in FIGS. 1 and 2, tubular treatment tool channels 107 and 108 into which an endoscopic treatment tool for treatment in the body can be inserted are disposed in the tip constructing portion 102, the curving mechanism 105, and the flexible tube portion 106. Distal ends of the treatment tool channels 107 and 108 are opened at the distal end of the tip constructing portion 102. The number of treatment tool channels 107 and 108 disposed in the endoscope device 100 is not particularly limited. In this embodiment, an example in which two treatment tool channels 107 and 108 (a first channel 107 and a second channel 108) are provided is described.

The tip constructing portion 102 is provided with an imaging unit (observation optical system) 103 and an illumination unit 104 in addition to the openings at the distal ends of the first channel 107 and the second channel 108. The imaging unit 103 includes an optical system and an image sensor for observing a treatment target. The illumination unit 104 irradiates the treatment target with illumination light when the treatment target is observed.

The curving mechanism 105 is disposed on the distal end side of the flexible tube portion 106. The curving mechanism 105 is a tubular member which can be curved as a whole and in which a plurality of curved segments or joint rings (hereinafter referred to as "joint rings and the like") formed in a ring shape is bendably connected to each other. Distal ends of a plurality of (four in this embodiment) angle wires (wire members, not shown) are connected to the distal end of the curving mechanism 105. The curving mechanism 105 can be curved by an operation of pulling the angle wires to proximal end sides. The proximal ends of the angle wires are disposed in the manipulation section 110 to be described later.

The flexible tube portion 106 is a flexible tube through which the angle wires, wires for the imaging unit 103 and the illumination unit 104, and the like are disposed. The manipulation section 110 at least includes knobs for pulling the angle wires to the proximal end sides.

The configuration of the overtube (medical device) 1 will be described below. As shown in FIG. 1, the overtube 1 includes a long shaft member 2, a pair of wire guides (the support member, the first support member, the second support member) 3 and 4 (a first wire guide 3 and a second wire guide 4), treatment tool control wires (the linear member, the first linear member, the second linear member) 5 and 6 (a first control wire 5 and a second control wire 6), and an extension tube member (guide member) 9. The long shaft member 2 is formed in a tube shape and the insertion section 101 of the endoscope device 100 is inserted into the long shaft member. That is, the inner diameter of the long shaft member 2 is larger than the outer diameter of the insertion section 101. The pair of wire guides 3 and 4 is disposed on the outer surface or the inner surface of the long shaft member 2, or inside the long shaft member 2 along the longitudinal axis direction of the long shaft member 2. The treatment tool control wires 5 and 6 are inserted into the pair of wire guides 3 and 4, respectively. The extension tube member 9 is connected to the treatment tool control wires 5 and 6 and communicates with the first channel 107 or the second channel 108.

The long shaft member 2 is a flexible tube which is as long as or longer than the length of the pair of wire guides 3 and 4 from the distal end of the insertion section 101 in the endoscope device 100 and which is fixed in all of the forward and backward directions and the rotation direction and attached to the insertion section 101 to surround the insertion section 101 in the length range. For example, the long shaft member 2 has a size in the longitudinal direction in which the tip constructing portion 102, the curving mechanism 105, and the flexible tube portion 106 in the endoscope device 100 can be accommodated and is configured to be fixed to the flexible tube portion 106 at the proximal end of the flexible tube portion 106, at the distal end of the flexible tube portion 106, or at an arbitrary position within the entire length of the flexible tube portion 106.

In the long shaft member 2, the position at which the curving mechanism 105 of the endoscope device 100 is disposed is a curved portion 2a which is deformable in a shape along the curved shape of the curving mechanism 105 by curving deformation of the curving mechanism 105.

As shown in FIG. 2, the pair of wire guides 3 and 4 are support members which support the pair of treatment tool control wires 5 and 6 (the first control wire 5 and the second control wire 6) at positions substantially along the angle wires for curving operation of the endoscope device 100 and parallel to the longitudinal axis of the endoscope device 100.

In the first wire guide 3, a first space extending along the extending direction of the longitudinal axis of the curved portion 2a is formed. The first control wire 5 is inserted into the first space. In the second wire guide 4, a second space extending along the extending direction of the longitudinal axis of the curved portion 2a is formed. The second control wire 6 is inserted into the second space.

The pair of wire guides 3 and 4 are disposed along the longitudinal axis of the curved portion 2a at positions separated outward in the radial direction of the extension tube member 9 from the outer side surface of the extension tube member 9. The pair of wire guides 3 and 4 are located at positions apart from the longitudinal axis of the curved portion 2a in the long shaft member 2. The pair of wire guides 3 and 4 has a length from the distal end of the insertion section 101 of the endoscope device 100 to at least a part of the curving mechanism 105 of the endoscope device 100. The pair of wire guides 3 and 4 may be formed of a metallic coil sheath, a resinous tube, a plurality of metallic or resinous rings separated from each other, or the like. In this embodiment, the pair of wire guides 3 and 4 can be stretchably/contractibly deformed in the direction of the longitudinal axis of the pair of wire guides 3 and 4 itself while maintaining a state in which the longitudinal axes of the pair of wire guides 3 and 4 are parallel to the longitudinal axis of the long shaft member 2.

The treatment tool control wires 5 and 6 are wires (linear members) for controlling the direction of the distal end of the treatment tool attached to the treatment tool channels 107 and 108 of the endoscope device 100. The distal end of the first control wire 5 has a first connection portion (connection portion) connected to the vicinity of the distal end of the extension tube member 9. The distal end of the second control wire 6 has a second connection portion (connection portion) connected to the vicinity of the distal end of the extension tube member 9. That is, the distal ends of the treatment tool control wires 5 and 6 are fixed to the vicinity of the distal end of the extension tube member 9.

The first control wire 5 protruding from the first wire guide 3 is inclined with respect to the longitudinal axis of the extension tube member 9. The first connection portion is connected to the extension tube member 9. The second control wire 6 protruding from the second wire guide 4 is inclined with respect to the longitudinal axis of the extension tube member 9. The second connection portion is connected to the extension tube member 9. The distance between the first connection portion and the second connection portion is smaller than the distance between the first wire guide 3 and the second wire guide 4 in a virtual plane perpendicular to the longitudinal axis of the curved portion 2a.

The proximal ends of the treatment tool control wires 5 and 6 are fixed to the long shaft member 2 at positions more proximal than the proximal ends of the wire guides 3 and 4. The proximal ends of the first control wire 5 and the second control wire 6 are disposed at positions facing each other in the radial direction of the long shaft member 2. In this embodiment, the length of the first control wire 5 and the length of the second control wire 6 are equal.

The extension tube member 9 is formed in a tube shape of which the proximal end can be fixed to the distal end of the first channel 107 or the second channel 108 and the internal space can communicate with any one of the first channel 107 and the second channel 108. A treatment tool which is inserted through the first channel 107 or the second channel 108 can pass through the extension tube member 9. The extension tube member 9 serves as a guide member that holds a treatment tool by allowing the treatment tool to be inserted thereinto. When the treatment tool which is inserted through the first channel 107 or the second channel 108 is inserted into the extension tube member 9, the extension tube member 9 has a positional relationship in which it extends from the distal end of the curved portion 2a. The central axis of the extension tube member 9 is substantially parallel to the central axis of the first wire guide 3 and the central axis of the second wire guide 4 and is apart from the central axis of the first wire guide 3 and the central axis of the second wire guide 4. The extension tube member 9 has flexibility.

When the extension tube member 9 is fixed to the distal end of the first channel 107, the extension tube member 9 is a tubular member extending the first channel 107 to the distal side. When the extension tube member 9 is fixed to the distal end of the second channel 108, the extension tube member 9 is a tubular member extending the second channel 108 to the distal side. That is, the extension tube member 9 according to this embodiment is a channel-extension tube extending any one of the two treatment tool channels 107 and 108 of the endoscope device 100.

When any one of the first control wire 5 and the second control wire 6 is pulled to the proximal end, the extension tube member 9 can be curved to the pulled side and can curve the treatment tool which is inserted into the extension tube member 9.

Figure 4:
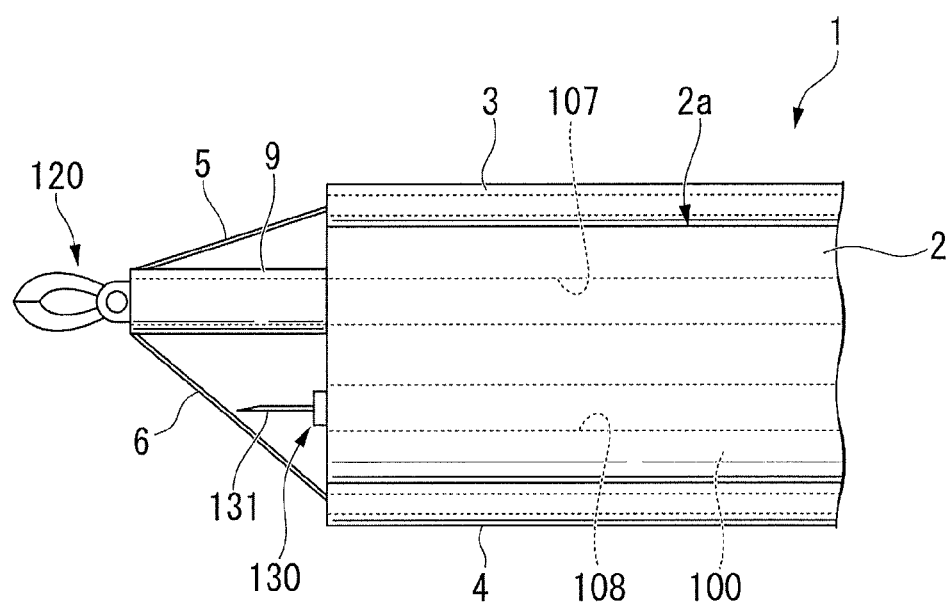
FIG. 4 is a diagram showing a process in use of the overtube.
Figure 5:
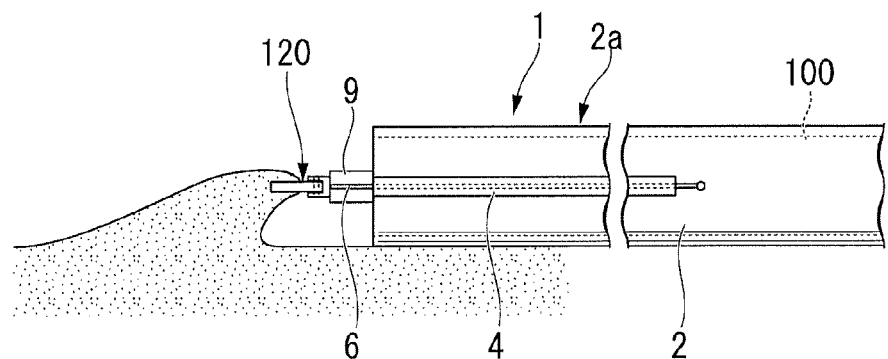
FIG. 5 is a side view showing an operation of the overtube.
Figure 6:
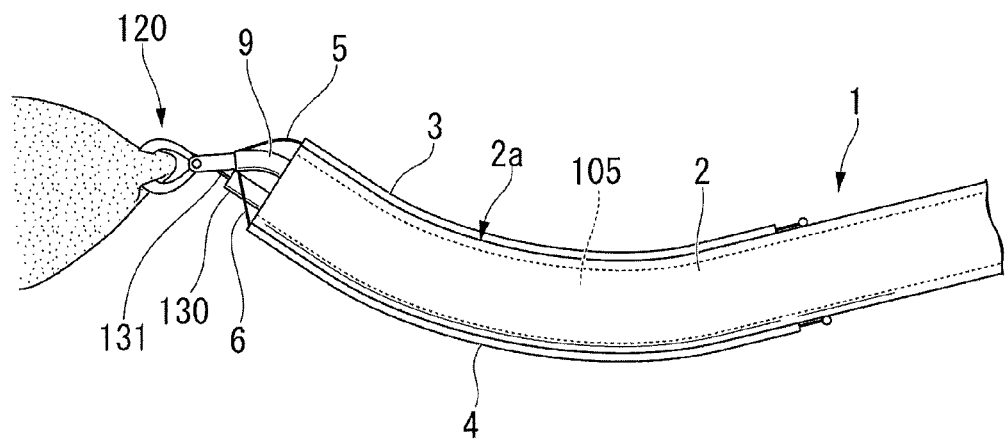
FIG. 6 is a top view showing an operation of the overtube.
Figure 7:
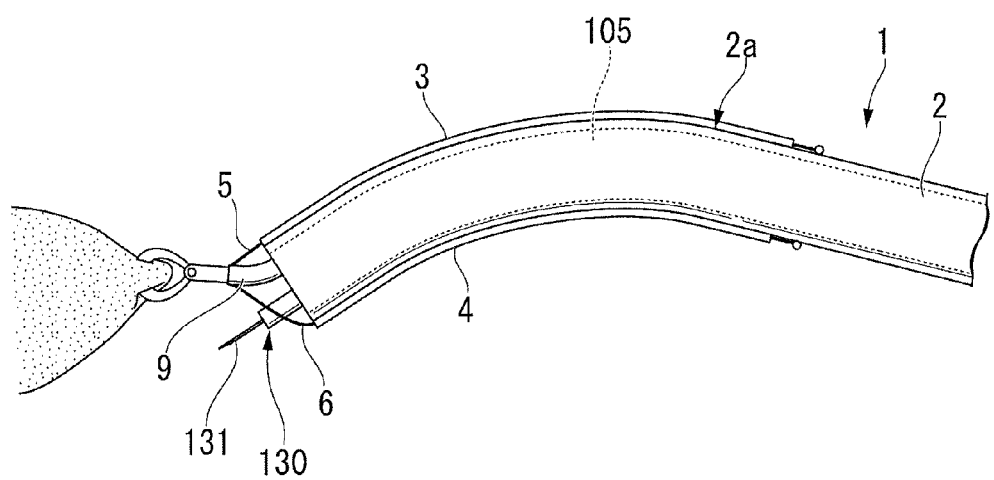
FIG. 7 is a top view showing an operation of the overtube.

The operation of the overtube 1 according to this embodiment will be described below. FIG. 4 is a diagram showing a process in use of the overtube 1. FIGS. 5 to 7 are diagrams showing the operation of the overtube 1. In the following description, the operation of the overtube 1 will be described with reference to the usage of the overtube 1 in endoscopic submucosal dissection. The overtube 1 according to this embodiment is applied not only to a specific procedure but also to other procedures.

First, the overtube 1 is attached to the endoscope device 100 before the endoscope device 100 is inserted into a body. Specifically, the long shaft member 2 is put on the distal end side of the insertion section 101 of the endoscope device 100. The proximal end side of the long shaft member 2 is fixed to the insertion section 101 or the manipulation section 110 of the endoscope device 100 in all of the forward and backward directions and the rotation direction. The proximal end of the extension tube member 9 is fixed to the distal end of any one of the first channel 107 and the second channel 108 and the internal space of the extension tube member 9 communicates with the opening of the distal end thereof (the proximal end of the extension tube member 9 is fixed to the distal end of the first channel 107 and the extension tube member 9 communicates with the first channel 107 in this embodiment). In this procedure, as shown in FIG. 3, the long shaft member 2 is positioned with respect to the insertion section 101 of the endoscope device 100 such that the first control wire 5 and the second control wire 6 are arranged in the right and left curving direction (which is the direction indicated by reference sign X in FIG. 3 and which is substantially the same as the right-left direction of an image acquired by the imaging unit 103) of the curving mechanism 105 of the endoscope device 100.

Subsequently, the insertion section 101 of the endoscope device 100 is inserted into a body and the distal end of the insertion section 101 is introduced to a treatment target portion. If necessary, the treatment target portion is observed using the endoscope device 100. In the endoscopic submucosal dissection, an excision target tissue is marked using a known method, then the incision is started from the periphery of the excision target tissue, and a submucosal layer is dissected while elevating the target tissue, whereby a lesion is excised.

In this embodiment, in performing the endoscopic submucosal dissection, as shown in FIG. 4, a grasping forceps 120 for grasping a lesion tissue is inserted into the first channel 107 to which the extension tube member 9 is attached and the grasping forceps 120 is caused to protrude from the opening at the distal end of the extension tube member 9. A known endoscopic incision tool 130 suitable for dissecting a submucosal layer is inserted into the second channel 108 to which the extension tube member 9 is not attached. The insertion of the treatment tool or the like into the endoscope device 100 may be performed after the endoscope device 100 is inserted into a patient's body and the tip constructing portion 102 reaches a target portion, or may be performed in advance before the tip constructing portion 102 reaches a target portion or before the endoscope device 100 is inserted into a patient's body.

In the step of dissecting the submucosal layer, first, as shown in FIG. 5, an excision target tissue is elevated using the grasping forceps 120. The elevating of the tissue is carried out by vertically curving the curving mechanism 105 of the endoscope device 100. Accordingly, the submucosal layer to be dissected enters the field of view of the imaging unit 103 of the endoscope device 100.

Subsequently, in order to dissect the submucosal layer, the excision target portion is excised using a knife edge 131 of the endoscopic incision tool 130 by causing the endoscopic incision tool 130 to protrude from the distal end of the treatment tool channel 108 and curving the curving mechanism 105 of the endoscope device 100. Specifically, the curving mechanism 105 is curved in the right-left direction (the direction indicated by reference sign X in FIG. 3) of the field of view of the imaging unit 103 of the endoscope device 100, or the flexible tube portion 106 is rotated about the longitudinal axis of the flexible tube portion 106. At this time, as shown in FIG. 6, the outer portion of the curved shape of the curving mechanism 105 in a curved state is stretched more than that in a state in which the curving mechanism 105 is in a straight state, and the inner portion of the curved shape of the curving mechanism 105 in the curved state is shortened more than that in a state in which the curving mechanism 105 is in a straight state. That is, on the outer portion of the curved shape of the curving mechanism 105 in a curved state, a length measured parallel to the central axis of the curving mechanism 105 is longer than a length of the inner portion of the curved shape of the curving mechanism 105 in the curved state.

Here, in the overtube 1 attached to the insertion section 101 of the endoscope device 100, the long shaft member 2 is curved in a shape along the curved deformation of the curving mechanism 105. However, a force for stretching or shortening the treatment tool control wires 5 and 6 is not applied to the treatment tool control wires 5 and 6 inserted into the wire guides 3 and 4 fixed to the outer surface of the long shaft member 2.

Accordingly, when the curving mechanism 105 is in a curved state, one of the treatment tool wires 5 and 6 located on the outer portion of the curved shape of the curving mechanism 105 in the curved state acts to pull the distal end of the extension tube member 9 to the proximal side. The other of the treatment tool wires 5 and 6 located on the inner portion of the curved shape of the curving mechanism 105 in the curved state is loosened to allow pulling of the extension tube member 9 by the treatment tool control wire 5 or 6 on the outer portion of the curved shape. Accordingly, the extension tube member 9 is curved in the direction of the treatment tool control wire 5 or 6 located on the outer portion of the curved shape of the curving mechanism 105 in the curved state.

In this way, in this embodiment, when the curving mechanism 105 is curved, the extension tube member 9 can be curved in the opposite direction to the curving direction and it is thus possible to change the direction of the treatment tool or the like (the grasping forceps 120 in this embodiment) inserted into the extension tube member 9, In the step of dissecting the submucosal layer while repeating the curving operation of the endoscope device 100 in the right-left direction in the field of view of the imaging unit 103 of the endoscope device 100, the extension tube member 9 is curved in the direction opposite to the curving mechanism 105 to cancel the curving motion of the curving mechanism 105 as shown in FIG. 7. Accordingly, the position of the distal end of the extension tube member 9 is not moved greatly even when the curving mechanism 105 is curved in the right-left direction. As a result, the excision target tissue grasped by the grasping forceps 120 inserted into the extension tube member 9 is not moved greatly in the step of dissecting the submucosal layer.

In a medical device used for the endoscopic submucosal dissection in the related art, a grasping forceps for elevating an excision target tissue and an endoscopic incision tool for dissecting a submucosal layer are attached to a single endoscope device. Accordingly, when the endoscopic incision tool is moved to dissect the submucosal layer, the grasping forceps grasping the excision target tissue may also be moved together. As a result, a high level of skill is required for rapidly dissecting a submucosal layer while maintaining an appropriate elevated state.

On the other hand, since the overtube 1 according to this embodiment is configured such that the extension tube member 9 is curved in the opposite direction to the curving motion of the curving mechanism 105, the movement of the endoscopic incision tool 130 for dissecting a submucosal layer and the movement of the grasping forceps 120 for grasping an excision target tissue are not linked with each other and the procedure of rapidly dissecting the submucosal layer while maintaining an appropriate elevated state can be easily performed.

Since the extension tube member 9 can be curved in the opposite direction to the curving motion of the curving mechanism 105 by pulling the distal end of the extension tube member 9 using the treatment tool control wires 5 and 6 disposed on the outer surface of the long shaft member 2 along the direction of the longitudinal axis of the long shaft member 2, a mechanism configured to curve the extension tube member 9, the mechanism which has a simple structure and curves the extension tube member 9 accurately and oppositely linking with the curved state of the endoscope device 100 can be obtained.

An operator such as a practitioner or a caregiver does not have to perform an additional manipulation for manipulating the extension tube member 9. Accordingly, even when treatment in which the manipulation of the endoscope device 100 is complicated is performed, the burden on the operator does not excessively increase and the treatment can be easily learned by the operator.

Since the overtube 1 employs a configuration in which the extension tube member 9 is curved by the power used for curving the curving mechanism 105, an actuator or other power source for curving the extension tube member 9 is not necessary and it is thus possible to manufacture the overtube with a simple structure at a low cost.

Figure 8:
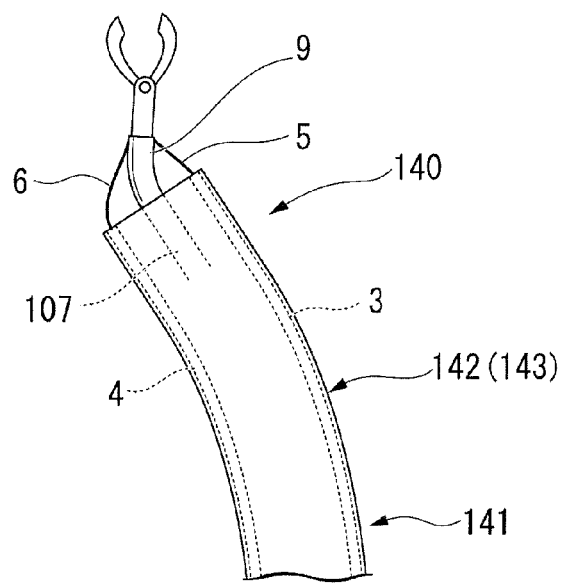
FIG. 8 is a perspective view showing an example of a design modification of the medical device according to the first embodiment of the present invention.
Figure 9:
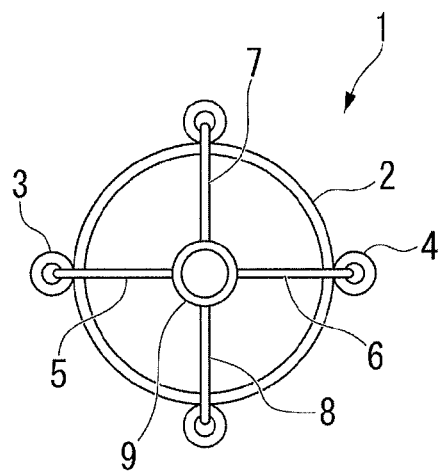
FIG. 9 is a front view showing an example of another design modification of the medical device according to the first embodiment of the present invention.
Figure 10:
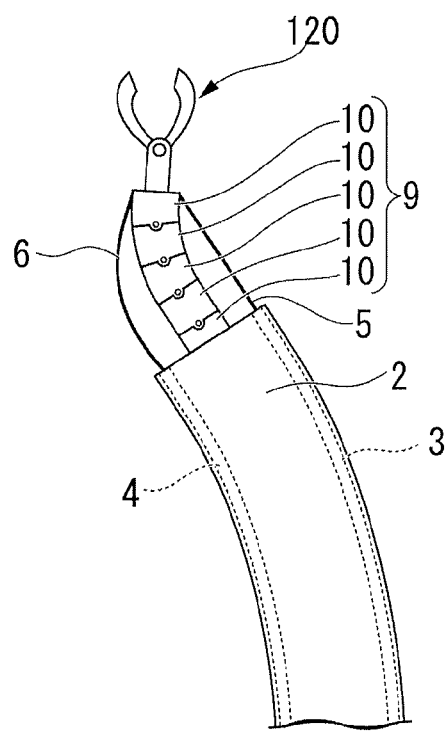
FIG. 10 is a side view showing an example of still another design modification of the medical device according to the first embodiment of the present invention.

An example of a design modification of the medical device according to the present embodiment will be described below. FIG. 8 is a perspective view showing an example of a design modification of the medical device according to this embodiment. FIG. 9 is a front view showing an example of another design modification of the medical device according to this embodiment. FIG. 10 is a side view showing an example of still another design modification of the medical device according to this embodiment.

As shown in FIG. 8, the medical device according to this embodiment may be an endoscope device 140 including the pair of wire guides 3 and 4, the pair of treatment tool control wires 5 and 6, and the extension tube member 9 which are disposed in the overtube 1. The endoscope device 140 further includes an insertion section 141, a curved portion 142, a curving mechanism 143, and the treatment tool channel 107 (identical to the treatment tool channel 107 of the endoscope device 100). The insertion section 141 is inserted into a body. The curving portion 142 can be curved similarly to the curved portion 2a of the long shaft member 2 and is disposed at the distal end of the insertion section 141. The curving mechanism 143 actively curves the curved portion 142.

In this case, the pair of wire guides 3 and 4 and the pair of treatment tool control wires 5 and 6 are disposed in the vicinity of angle wires (wire members, not shown) for pulling the curving mechanism 143 in the right-left direction in the endoscope device 140 and inside the outer circumferential surface of the insertion section 141 of the endoscope device 140. The pair of wire guides 3 and 4 and the pair of treatment tool control wires 5 and 6 may be disposed outside the outer circumferential surface of the insertion section 141 of the endoscope device 140. In the endoscope device 140 including the extension tube member 9, the configuration of the extension tube member 9 may be replaced by extending the treatment tool channel 107 to the distal side.

The medical device according to this embodiment may not include the extension tube member 9 and may be configured such that the distal ends of the treatment tool control wires 5 and 6 can be fixed to the treatment tool or the like itself inserted into the treatment tool channels 107 and 108 of the endoscope device 100. In this case, the treatment tool or the like inserted into the treatment tool channels 107 and 108 of the endoscope device 100 may be provided with a receiving portion to and from which the distal ends of the treatment tool control wires 5 and 6 are attached and detached. When the distal ends of the treatment tool control wires 5 and 6 are directly fixed to the treatment tool or the like, the replacement of the treatment tool or the like in the endoscope device 100 can be done by attaching and detaching the distal ends of the treatment tool control wires 5 and 6 in a state in which the endoscope device 100 is out of a patient's body. The distal ends of the treatment tool control wires 5 and 6 may always be fixed to the treatment tool or the like without considering the replacement of the treatment tool during treatment.

As shown in FIG. 9, as a design modification of the overtube 1 which can be attached to the endoscope device 100, four treatment tool control wires 5, 6, 7, and 8 may be disposed at positions apart from one another by 90° in the circumferential direction of the insertion section 101 of the endoscope device 100, and the distal ends of the treatment tool control wires 5, 6, 7, and 8 may be fixed to the distal end of the extension tube member 9. In this case, the extension tube member 9 can be curved in the opposite direction to the curving motion in all four directions of up-and down direction and left-and right direction in the curving mechanism 105.

As shown in FIG. 10, the extension tube member 9 may not be a simple flexible tube but may have a joint structure 10 in which the curving direction is regulated in a predetermined direction. In this case, the extension tube member 9 is not bent easily even when a force for bending the extension tube member 9 in a direction other than the predetermined direction is applied by the treatment tool or the like inserted into the extension tube member 9.

The overtube 1 according to this embodiment can be used for a procedure other than the procedure of endoscopic submucosal dissection. For example, by using the overtube 1, movement of a viewpoint such as observing a side portion of a tissue becomes possible while the tissue is elevated. In this case, a plurality of treatment tool channels does not need to be disposed in the endoscope device 100.

(Second Embodiment)

Figure 11:
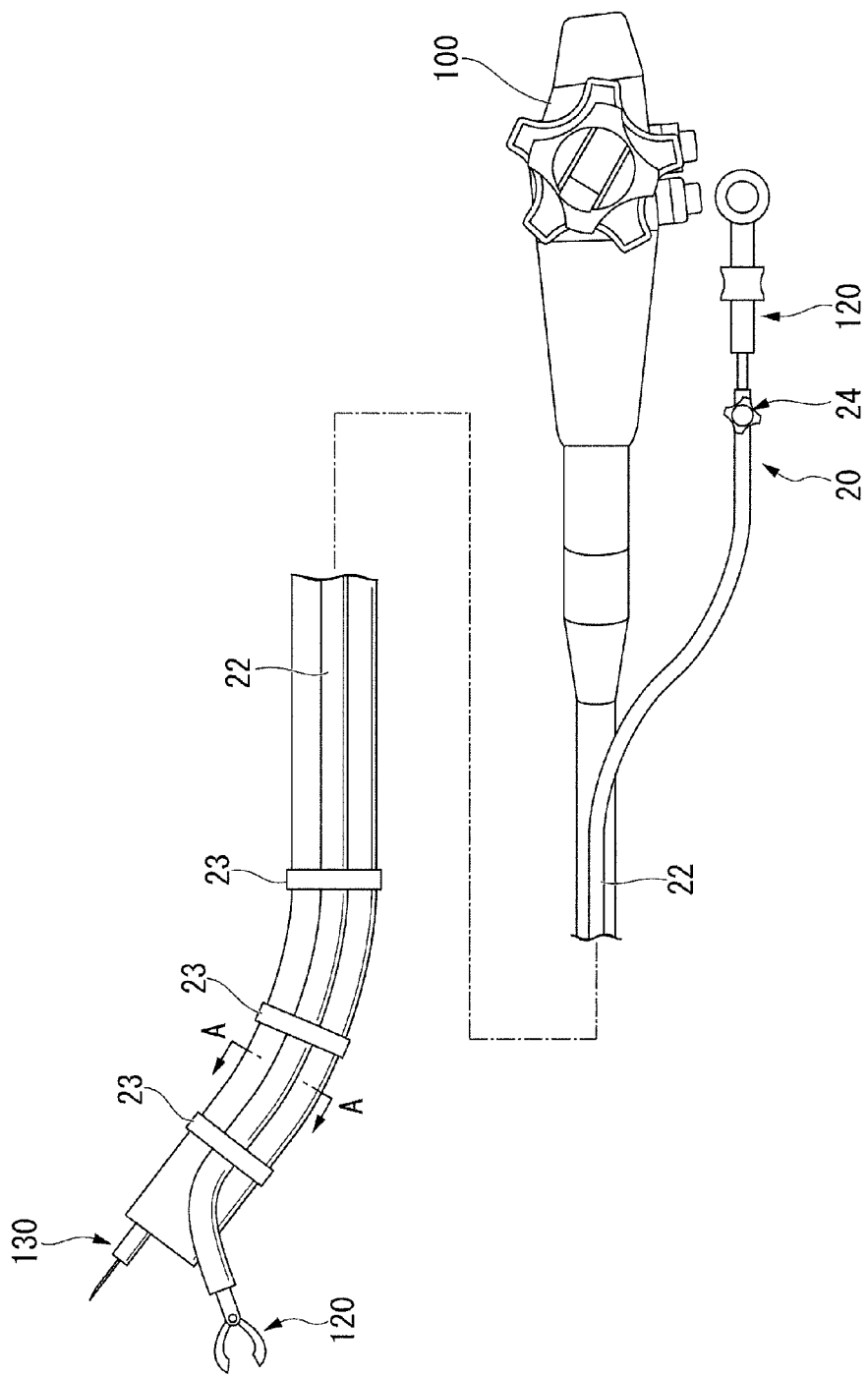
FIG. 11 is a general view of an external treatment tool as a medical device according to a second embodiment of the present invention.
Figure 12:
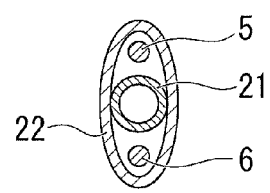
FIG. 12 is a cross-sectional view taken along line A-A in FIG. 11.

A second embodiment of the present invention will be described below. FIG. 11 is a general view of an external treatment tool 20 as a medical device according to the second embodiment of the present invention. FIG. 12 is a cross-sectional view taken along line A-A in FIG. 11. The same components as in the first embodiment will be referenced by the same reference signs and description made in the first embodiment will not be repeated.

As shown in FIG. 11, the external treatment tool 20 according to this embodiment can be attached to the endoscope device 100.

The structure of the endoscope device to which the external treatment tool 20 according to this embodiment is attached is not particularly limited. In the following description, an example in which the external treatment tool 20 is attached to the endoscope device 100 according to the first embodiment will be described.

As shown in FIGS. 11 and 12, the external treatment tool (medical device) 20 includes an inner sheath 21, an outer sheath 22, the treatment tool control wires (linear member, first linear member, second linear member) 5 and 6 (a first control wire 5 and a second control wire 6), and a plurality of bands 23. The inner sheath 21 includes a channel into which a treatment tool is inserted. The outer sheath 22 is formed in a tube shape and the inner sheath 21 is inserted thereinto. The treatment tool control wires 5 and 6 are disposed between the inner sheath 21 and the outer sheath 22. The plurality of bands 23 fixes the outer sheath 22 to the insertion section 101 of the endoscope device 100. In this embodiment, the proximal end of the external treatment tool 20 is provided with an adjuster 24 for moving the treatment tool control wires 5 and 6. The external treatment tool 20 is fixed to the outside of the endoscope device 100.

The first control wire 5 and the second control wire 6 are held at positions facing each other on the outer surface of the inner sheath 21 and are disposed to extend in parallel to the central axis of the inner sheath 21. The distal ends of the first control wire 5 and the second control wire 6 are fixed to the distal end of the inner sheath 21 or the distal end of the outer sheath 22. As for the plurality of bands 23, at least one band is disposed at the distal end of the curving mechanism 105 of the endoscope device 100 and at least one band is disposed at the proximal end of the curving mechanism 105.

In this embodiment, by the same principle as described in the first embodiment, when the curving mechanism 105 of the endoscope device 100 is curved, the outer portion of the curve becomes longer than the inner portion of the curve and thus a part of the external treatment tool 20 closer to a distal end than the band 23 disposed closest to the distal end is curved in the opposite direction to the curving direction of the curving mechanism 105 of the endoscope device 100. The part closer to the distal end than the band 23 closest to the distal end can be curved along the curving shape of the curving mechanism 105 of the endoscope device 100 by adjusting the positions of the first control wire 5 and the second control wire 6 using the adjuster 24.

In this embodiment, the same procedure as in the first embodiment can be carried out by attaching the grasping forceps 120 to the inner sheath 21 of the external treatment tool 20 and attaching the endoscopic incision tool 130 to the treatment tool channel of the endoscope device 100.

Figure 13:
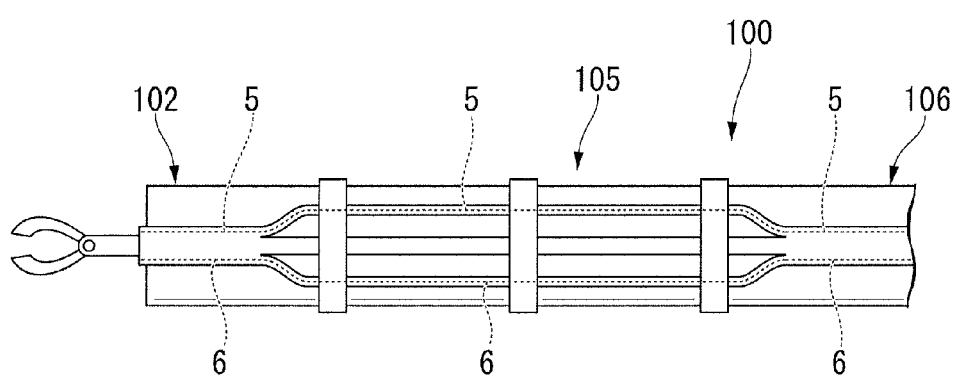
FIG. 13 is a side view showing an example of a design modification of the medical device according to the second embodiment of the present invention.

Next, an example of a design modification of the medical device according to the present embodiment will be described. FIG. 13 is a side view showing an example of a design modification of the medical device according to this embodiment. As shown in FIG. 13, for example, the distance between the first control wire 5 and the second control wire 6 may be set to be larger in a section in which the curving mechanism 105 of the endoscope device 100 is located. Accordingly, the difference in length between the outer circumference and the inner circumference of the curve further increases. The distance between the first control wire 5 and the second control wire 6 may be set to be smaller in a section in which the flexible tube portion 106 of the endoscope device 100 is located. Accordingly, it is possible to reduce an influence of the curving of the flexible tube portion 106 which is not associated with the curving of the curving mechanism 105.

The same advantages can be obtained even by inserting the external treatment tool 20 into the treatment tool channels 107 and 108 of the endoscope device 100 instead of fixing the external treatment tool 20 to the outer surface of the insertion section 101 of the endoscope device 100 using the bands 23.

The configuration identical to the adjuster described in this embodiment may be provided in the overtube according to the first embodiment.

While favorable embodiments of the present invention have been described above, the present invention is not limited to these embodiments. Addition, omission, replacement, and other modifications of elements can be made in the present invention without departing from the gist of the present invention. The present invention is not limited to the above description, and is defined only by the appended claims.

What is claimed is:

1. A medical device comprising;
a long shaft member configured to be inserted into a body;
a curved portion that is disposed at a distal end of the long shaft member, the curved portion being configured to bend;
a first support member and a second support member that are each formed on an outer surface of the long shaft member along the curved portion, each of the first support member and the second support member has a space extending along a longitudinal axis of the curved portion, the first support member and the second support member being configured to deform along a curved shape of the curved portion;
a guide member that extends from a distal end of the curved portion on an axis line substantially parallel to a central axis of the support member, the guide member having a space into which a treatment tool is inserted, a central axis of the guide member being positioned apart from the central axis of the support member; and
a first linear member and a second linear member that each includes a connection portion connected to the guide member at a distal end of each of the first linear member and the second linear member, each of the first linear member and the second linear member includes a proximal end fixed to the long shaft member, the first linear member and the second linear member each being inserted into the space of the first support member and the second support member, the first linear member and the second linear member each pulling the guide member in accordance with a change of the curved shape by bending the curved portion, the bending of the curved portion in a first direction causing corresponding bending of the guide member in a second direction, which is opposite to the first direction, due to tension applied by one of the first linear member and the second linear member to the guide member, the first linear member and the second linear member each protruding from the first support member and the second support member and being inclined with respect to a longitudinal axis of the guide member.

2. The medical device according to claim 1, wherein the long shaft member has a tube shape.

3. The medical device according to claim 1, wherein the long shaft member is an insertion section of an endoscope device.

4. The medical device according to claim 1, wherein:
the guide member is an extension tube member that has an outer diameter smaller than an outer diameter of the curved portion, the guide member being formed in a tube shape, and
the distal end of each of the first linear member and the second linear member is fixed to an outer side surface of the extension tube member.

5. The medical device according to claim 1, wherein:
the first support member is disposed along the longitudinal axis of the curved portion at a first position which is separated outward in a radial direction of the guide member from an outer side surface of the guide member,
the second support member is disposed along the longitudinal axis of the curved portion at a second position which is different from the first position and which is separated outward in the radial direction of the guide member from the outer side surface of the wide member, and
a distance between the connection portion of the first linear member and the connection portion of the second linear member is smaller than a distance between the first position and the second position in a virtual cross-section of the curved portion perpendicular to the longitudinal axis of the curved portion.

6. The medical device according to claim 1, wherein the proximal end of each of the first linear member and the second linear member is fixed to the long shaft member.

7. The medical device according to claim 3, wherein each of the first linear member and the second linear member has a length from a distal end of the insertion section to at least a part of a curving mechanism which is a part of the curved portion and which can be curved as a whole.

* * * * *